(12) United States Patent
Robertson et al.

(10) Patent No.: US 11,639,878 B2
(45) Date of Patent: *May 2, 2023

(54) WAIST MEASURING BELT

(71) Applicant: eBay Inc., San Jose, CA (US)

(72) Inventors: Jennifer Robertson, Cedar Park, TX (US); Bryant Genepang Luk, Round Rock, TX (US); Robert He, Pflugerville, TX (US); Ananya Das, Austin, TX (US); Christopher Diebold O'Toole, Cedar Park, TX (US); Yu Tang, Round Rock, TX (US); Richard Chapman Bates, Austin, TX (US); Jason Ziaja, Cedar Park, TX (US)

(73) Assignee: eBay Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/684,737

(22) Filed: Mar. 2, 2022

(65) Prior Publication Data

US 2022/0187150 A1 Jun. 16, 2022

Related U.S. Application Data

(63) Continuation of application No. 17/081,822, filed on Oct. 27, 2020, now Pat. No. 11,300,465, which is a
(Continued)

(51) Int. Cl.
*A41F 9/00* (2006.01)
*A61B 5/107* (2006.01)
(Continued)

(52) U.S. Cl.
CPC .............. *G01L 5/047* (2013.01); *A41F 9/002* (2013.01); *A41H 1/02* (2013.01); *A61B 5/0004* (2013.01);
(Continued)

(58) Field of Classification Search
CPC ....... G01L 5/047; B60N 2/0248; A41F 9/002; A41H 1/02; A44B 11/005; G01B 3/11;
(Continued)

(56) References Cited

U.S. PATENT DOCUMENTS 4,473,949 A 10/1984 Schechtman
5,558,370 A 9/1996 Behr
(Continued)

OTHER PUBLICATIONS

U.S. Appl. No. 14/556,522, "Advisiory Action Received for U.S. Appl. No. 14/556,522 dated Jan. 24, 2019", dated Jan. 24, 2019, 2 Pages.
(Continued)

*Primary Examiner* — Ly D Pham
(74) *Attorney, Agent, or Firm* — FIG. 1 Patents

(57) ABSTRACT

In various example embodiments, devices, systems, and methods for a waist measuring belt are provided. An example waist measuring belt is made up of a belt buckle frame with attachments for a belt strap. The belt further includes a position measuring module coupled to the belt buckle frame that measures an attachment position of a second end of the belt strap to the belt buckle frame. The belt also includes a tension measuring module coupled to the belt buckle frame that measures a tension through the belt buckle frame and the belt strap. A memory and a wireless communication module attached to the belt may be used to store measurements and communicate with a mobile device or server. In various embodiments, estimated user waist sizes over time using measured values and belt-specific data may be used to estimate a user's waist size and generate a waist size history.

20 Claims, 12 Drawing Sheets

Related U.S. Application Data continuation of application No. 16/433,052, filed on Jun. 6, 2019, now Pat. No. 10,845,260, which is a continuation of application No. 14/556,522, filed on Dec. 1, 2014, now Pat. No. 10,359,327.

(51) Int. Cl.

| | |
|---|---|
| *G01L 5/04* | (2006.01) |
| *A41H 1/02* | (2006.01) |
| *G01B 3/11* | (2006.01) |
| *A61B 5/00* | (2006.01) |
| *A44B 11/00* | (2006.01) |
| *G01B 21/02* | (2006.01) |
| *G01B 21/04* | (2006.01) |
| *B60N 2/02* | (2006.01) |

(52) U.S. Cl.
CPC .............. *A61B 5/1072* (2013.01); *G01B 3/11* (2013.01); *A44B 11/005* (2013.01); *A61B 5/107* (2013.01); *A61B 5/6823* (2013.01); *A61B 5/6831* (2013.01); *B60N 2/0248* (2013.01); *G01B 21/02* (2013.01); *G01B 21/047* (2013.01)

(58) Field of Classification Search
CPC .... G01B 21/02; G01B 21/047; A61B 5/0004; A61B 5/1072; A61B 5/107; A61B 5/6823; A61B 5/6831
USPC .......................................................... 702/159
See application file for complete search history.

(56) References Cited

U.S. PATENT DOCUMENTS

| | | | |
|---|---|---|---|
| 5,784,676 | A | 7/1998 | Iseki |
| 5,877,431 | A | 3/1999 | Hirano |
| 10,359,327 | B2 | 7/2019 | Brenner et al. |
| 10,845,260 | B2 | 11/2020 | Robertson et al. |
| 11,300,465 | B2 | 4/2022 | Robertson et al. |
| 2004/0130737 | A1 | 7/2004 | Kamimura et al. |
| 2004/0217583 | A1 | 11/2004 | Wang |
| 2005/0209061 | A1 | 9/2005 | Crawford et al. |
| 2007/0282505 | A1 | 12/2007 | Bolton et al. |
| 2008/0133051 | A1 | 6/2008 | Wallace et al. |
| 2008/0185095 | A1 | 8/2008 | Gutknecht |
| 2008/0287770 | A1 | 11/2008 | Kurzweil et al. |
| 2009/0234201 | A1 | 9/2009 | Huang et al. |
| 2010/0130885 | A1 | 5/2010 | Hamaguchi et al. |
| 2011/0006021 | A1 | 1/2011 | Constantine |
| 2011/0028875 | A1 | 2/2011 | Martínez Ferro et al. |
| 2011/0060215 | A1 | 3/2011 | Tupin et al. |
| 2011/0106492 | A1 | 5/2011 | Jang et al. |
| 2011/0295144 | A1 | 12/2011 | Murakawa et al. |
| 2012/0180197 | A1 | 7/2012 | Cosky |
| 2012/0220834 | A1 | 8/2012 | Wijesiriwardana |
| 2013/0331637 | A1 | 12/2013 | Greff |
| 2014/0009335 | A1 | 1/2014 | Park |
| 2014/0142652 | A1 | 5/2014 | Francois et al. |
| 2014/0154384 | A1 | 6/2014 | Vardakostas et al. |
| 2014/0303851 | A1 | 10/2014 | Nagasawa |
| 2015/0186609 | A1 | 7/2015 | Utter |
| 2015/0342518 | A1 | 12/2015 | Persidsky et al. |
| 2015/0374573 | A1 | 12/2015 | Horst et al. |
| 2016/0153853 | A1 | 6/2016 | Brenner et al. |
| 2016/0187819 | A1 | 6/2016 | Tajiri et al. |
| 2016/0306393 | A1 | 10/2016 | Huitema |
| 2016/0317866 | A1 | 11/2016 | Fung |
| 2017/0028901 | A1 | 2/2017 | Rollins et al. |
| 2017/0196752 | A1 | 7/2017 | Behnke et al. |
| 2019/0209891 | A1 | 7/2019 | Fung |
| 2019/0254419 | A1 | 8/2019 | Desroches et al. |
| 2019/0285491 | A1 | 9/2019 | Robertson et al. |
| 2021/0041315 | A1 | 2/2021 | Robertson et al. |

OTHER PUBLICATIONS

U.S. Appl. No. 14/556,522 , "Applicant-initiated Interview Summary received for U.S. Appl. No. 14/556,522, dated Sep. 11, 2018", dated Sep. 11, 2018, 3 Pages.
U.S. Appl. No. 14/556,522 , "Corrected Notice Of Allowability received for U.S. Appl. No. 14/556,522, dated Apr. 23, 2019", dated Apr. 23, 2019, 5 Pages.
U.S. Appl. No. 14/556,522 , "Final Office Action received for U.S. Appl. No. 14/556,522, dated Nov. 1, 2018", dated Nov. 1, 2018, 14 Pages.
U.S. Appl. No. 14/556,522 , "First Action Interview—Office Action Summary received for U.S. Appl. No. 14/556,522, dated Jul. 25, 2017", dated Jul. 25, 2017, 7 Pages.
U.S. Appl. No. 14/556,522 , "First Action Interview—Office Action Summary received for U.S. Appl. No. 14/556,522, dated Nov. 15, 2017", dated Nov. 15, 2017, 5 Pages.
U.S. Appl. No. 14/556,522 , "First Action Interview—Pre-interview Communication received for U.S. Appl. No. 14/556,522, dated Apr. 13, 2017", dated Apr. 13, 2017, 5 Pages.
U.S. Appl. No. 14/556,522 , "Non-Final Office Action received for U.S. Appl. No. 14/556,522, dated Mar. 19, 2018", dated Mar. 19, 2018, 16 Pages.
U.S. Appl. No. 14/556,522 , "Notice of Allowance Received for U.S. Appl. No. 14/556,522 dated Mar. 8, 2019", dated Mar. 8, 2019, 6 Pages.
U.S. Appl. No. 14/556,522 , "Response to Final Office Action filed on Jan. 14, 2019, for U.S. Appl. No. 14/556,522, dated Nov. 1, 2018", dated Jan. 14, 2019, 17 Pages.
U.S. Appl. No. 14/556,522 , "Response to First Action Interview— Office Action Summary filed on Sep. 25, 2017 for U.S. Appl. No. 14/556,522, dated Jul. 25, 2017", dated Sep. 25, 2017, 11 Pages.
U.S. Appl. No. 14/556,522 , "Response to First Action Interview Filed on Mar. 15, 2018 for U.S. Appl. No. 14/556,522 dated Nov. 15, 2017", dated Mar. 15, 2018, 12 Pages.
U.S. Appl. No. 14/556,522 , "Response to Non-Final Office Action filed on Sep. 12, 2018, for U.S. Appl. No. 14/556,522, dated Mar. 19, 2018", dated Sep. 12, 2018, 19 Pages.
U.S. Appl. No. 16/433,052 , "Amendment Under 37 CFR filed on Sep. 21, 2020 U.S. Appl. No. 16/433,052", dated Sep. 21, 2020, 8 Pages.
U.S. Appl. No. 16/433,052 , "Applicant Initiated Interview Summary Received for U.S. Appl. No. 16/433,052, dated Apr. 16, 2020", dated Apr. 16, 2020, 3 Pages.
U.S. Appl. No. 16/433,052 , "Final Office Action Received for U.S. Appl. No. 16/433,052, dated Jun. 16, 2020", dated Jun. 16, 2020, 15 Pages.
U.S. Appl. No. 16/433,052 , "Non Final Office Action Received for U.S. Appl. No. 16/433,052, dated Jan. 24, 2020", Jan. 24, 2020, 13 Pages.
U.S. Appl. No. 16/433,052 , "Notice Of Allowance received for U.S. Appl. No. 16/433,052, dated Aug. 19, 2020", dated Aug. 19, 2020, 5 Pages.
U.S. Appl. No. 16/433,052 , "PTO Response to rule 312 Communication Received for U.S. Appl. No. 16/433,052, dated Oct. 22, 2020", dated Oct. 22, 2020, 2 Pages.
U.S. Appl. No. 16/433,052 , "Response to Final Office Action Filed on Jul. 20, 2020, for U.S. Appl. No. 16/433,052, dated Jun. 16, 2020", dated Jul. 20, 2020, 18 Pages.
U.S. Appl. No. 16/433,052 , "Response to Non-Final Office Action filed on May 4, 2020 for U.S. Appl. No. 16/433,052, dated Jan. 24, 2020", dated May 4, 2020, 15 Pages.
U.S. Appl. No. 17/081,822 , "Non-final Office Action received for U.S. Appl. No. 17/081,822, dated Oct. 14, 2021", dated Oct. 14, 2021, 6 Pages.
U.S. Appl. No. 17/081,822 , "Notice Of Allowance received for U.S. Appl. No. 17/081,822, dated Jan. 20, 2022", dated Nov. 20, 2022, 5 Pages.

200

MEASURING DURING A FIRST TIME PERIOD, USING A TENSION MEASURING MODULE OF A BELT, A FIRST TENSION IN A BELT STRAP OF THE BELT
210

↓

MEASURING DURING THE FIRST TIME PERIOD, USING A POSITION MEASURING MODULE COUPLED TO THE BELT, A FIRST POSITION WHERE THE BELT STRAP CONNECTS TO THE BELT BUCKLE FRAME
220

↓

MEASURING, USING THE TENSION MEASURING MODULE, DURING A SECOND TIMER PERIOD DIFFERENT THAN THE FIRST TIME PERIOD, A SECOND TENSION IN THE BELT STRAP
230

↓

MEASURING, USING THE POSITION MEASURING MODULE, A SECOND POSITION WHERE THE BELT STRAP CONNECTS TO THE BELT BUCKLE FRAME DURING A SECOND TIME PERIOD
240

↓

COMMUNICATING, USING ONE OR MORE PROCESSORS AND A WIRELESS COMMUNICATION MODULE COUPLED TO THE BELT BUCKLE FRAME, THE FIRST TENSION, THE SECOND TENSION, THE FIRST POSITION, AND THE SECOND POSITION TO A FIRST DEVICE.
250

FIG. 2

WAIST MEASURING BELT

CLAIM OF PRIORITY

This Application is a continuation of and claims priority to U.S. application Ser. No. 17/081,822, filed Oct. 27, 2020, entitled "Waist Measuring Belt," which is a continuation of and claims priority to U.S. application Ser. No. 16/433,052, filed Jun. 6, 2019, now U.S. Pat. No. 10,845,260, entitled "Waist Measuring Belt," which is a continuation of and claims priority to U.S. application Ser. No. 14/556,522, filed Dec. 1, 2014, now U.S. Pat. No. 10,359,327, entitled "Waist Measuring Belt," the disclosures of which are hereby incorporated by reference in their entirety.

TECHNICAL FIELD

Embodiments of the present disclosure relate generally to wearable electronics, and, more particularly, to a belt system for automatically taking waist measurements, as well as associated systems for tracking waist measurements and generated waist measurement alerts over time.

BACKGROUND

Personal health and fitness is important from many different perspectives. This includes economic, interpersonal, lifespan, and other such perspectives. Waist size, in certain circumstances, may function as an indicator for fitness, and waist size is particularly associated with a number of negative health outcomes when a waist size becomes excessively large. Devices, systems, and methods for automatic waist measurements and tracking of waist measurements over time are disclosed herein.

BRIEF DESCRIPTION OF THE DRAWINGS

Various ones of the appended drawings merely illustrate example embodiments of the present disclosure and cannot be considered as limiting its scope.

FIG. 2 illustrates a method of waist measurement using a waist measuring belt, according to some example embodiments.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

This description relates to devices, systems, and methods for waist measurement using a waist measuring belt. In particular, a waist measuring belt is described which enables capability for measuring a perimeter of a belt based on a position of attachment between a belt strap and a belt buckle frame, and measuring a tension in the belt strap. The waist measuring belt also includes communication input and output components which enable wireless communications with other devices. The waist measuring belt may either store waist measurements locally or communicate the measurements to a mobile device or another computing device that may record a history of waist measurements. Additional system aspects may then analyze the waist measurements that occur over time and present this information to a user via an interface of a user device.

A "waist" as referred to herein may be used broadly to apply to any part of a person which may be fitted with a belt strap. In certain example embodiments, a waist will be any perimeter around a person's abdomen between the rib cage and the hips that may be encircled by a belt strap. In other example embodiments, the waist may be a perimeter including portions of a person's body outside the person's abdomen. In various embodiments, such a perimeter may be at the person's skin or slightly away from the person's skin as separated by clothing or structures in the belt or the person's shape that separate the belt strap from the user's skin.

"Tension" as referred to herein refers to a pulling force exerted by each end of an elongated object that may make up a belt strap. This belt or belt strap may include a string, cable, chain, leather strap, or any other such object that may make up a belt strap. Such a belt includes a belt buckle or belt buckle frame that may be used to connect two ends of such a belt strap, and may thus propagate the pulling force through a perimeter loop of a belt.

Figure 1A:
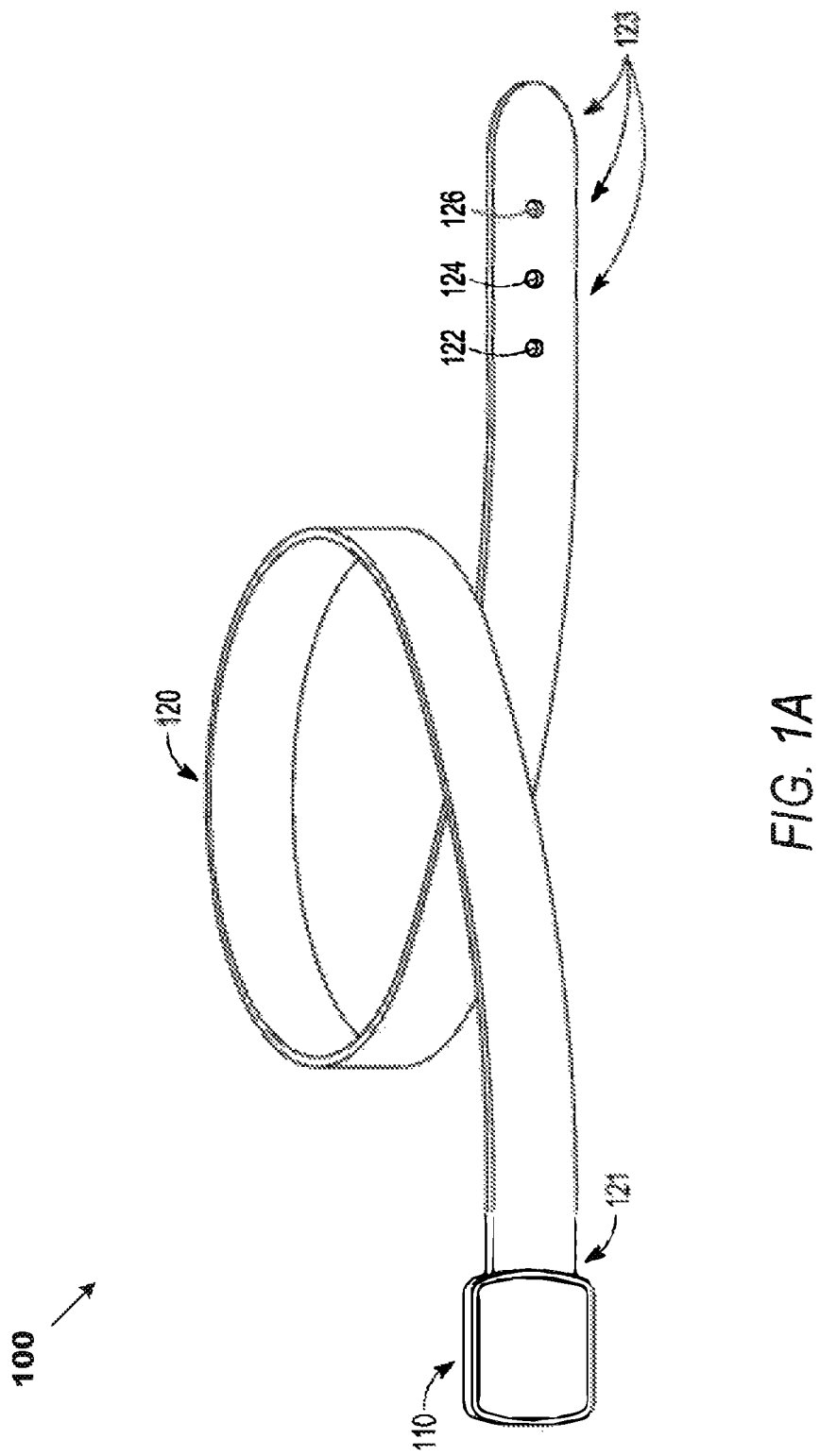
FIG. 1A illustrates a waist measuring belt, according to some example embodiments.
Figure 1B:
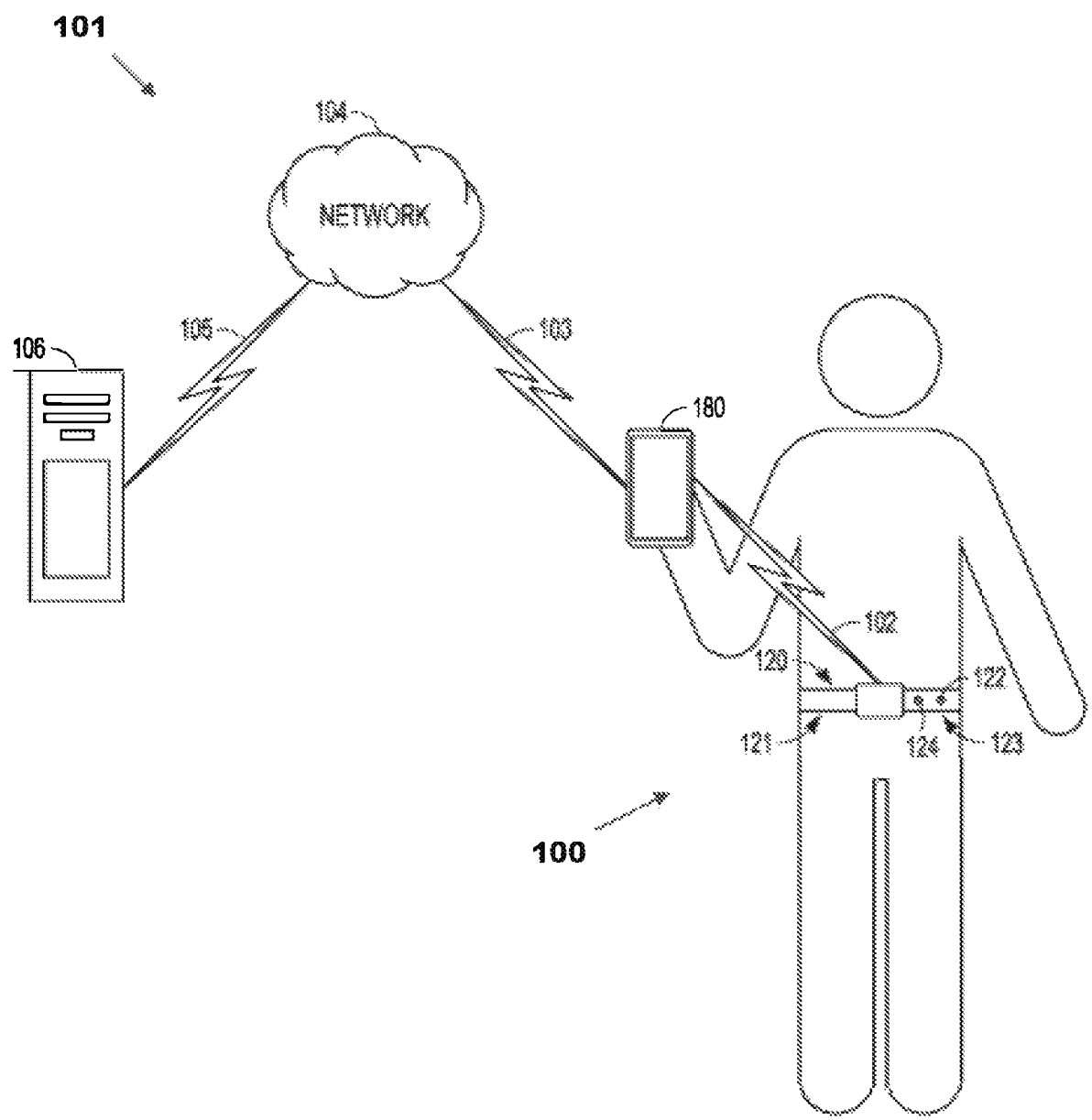
FIG. 1B illustrates an example embodiment of a system including a waist measuring belt.
Figure 1C:
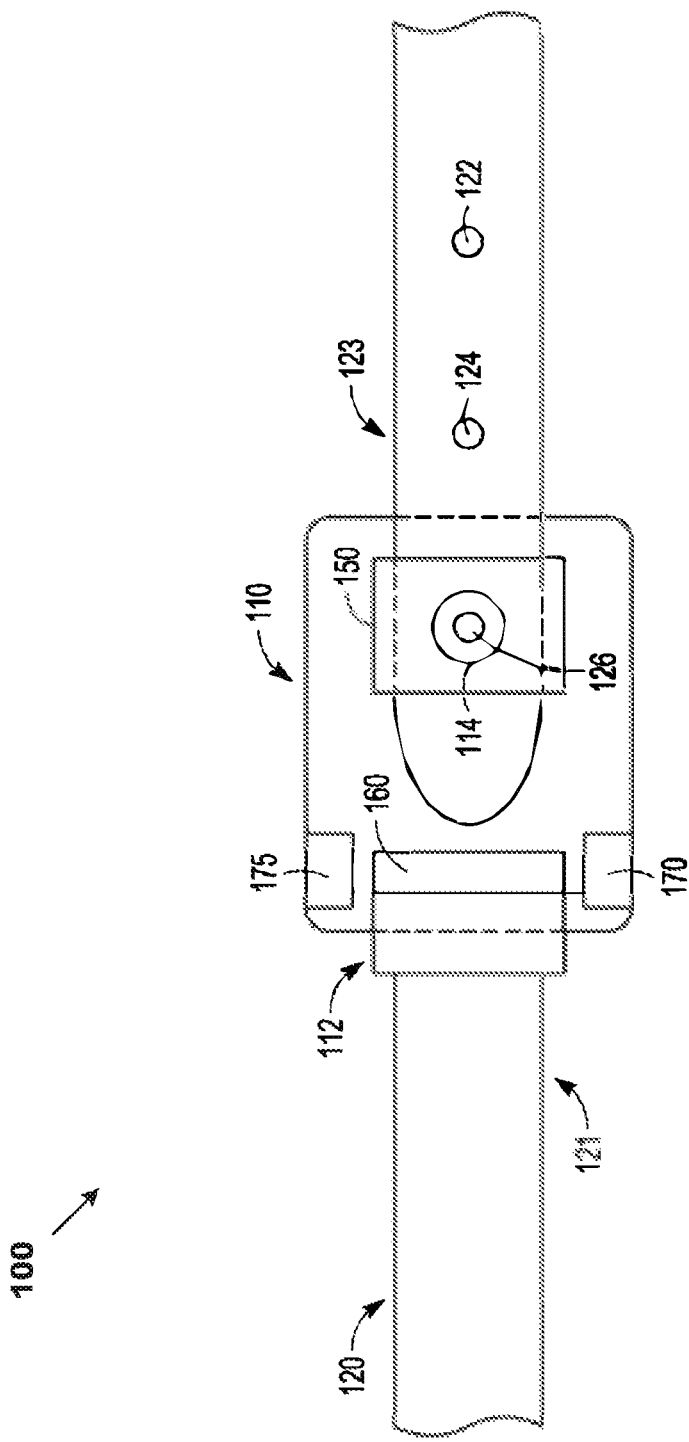
FIG. 1C illustrates additional aspects of a waist measuring belt, according to some example embodiments.

FIGS. 1A, 1B, and 1C illustrate aspects of a belt 100 for waist measurement according to some example embodiments. FIG. 1A illustrates the belt 100 in an open position. Belt 100 includes a belt buckle frame 110 and a belt strap 120. Such a belt buckle frame may be part of a belt buckle with an ornamental or protective from which may be permanently or modularly attacked to the belt buckle frame. In other embodiments, such a belt buckle frame may simply be a belt buckle. Belt strap 120 includes a first end 121 and a second end 123. Belt strap 120 also includes a plurality of attachment areas 122, 124, and 126.

FIG. 1B illustrates an example embodiment of a system 101 including the belt 100. System 101 includes not only belt 100 including elements 120-124 discussed above, but also mobile device 180, network 104, and server computer 106. In system 101, the belt 100 is in position around a user's waist, and may be taking waist measurements which include position measurements and tension measurements as detailed further below. Wireless input and output systems of belt 100 may provide communication with mobile device 180 via communication path 102 to enable waist measurement communications to be sent from belt 100 to mobile device 180. In other embodiments, belt 100 may communicate directly with network 104 via access points or other such wireless interfaces. Network 104 enables communication between mobile device 180 and server computer 106 via communication path 103, the network 104, and communication path 105. This may include any wired or wireless communication means and any network devices such as access points, routers, intermediate server systems, or any other such network communication device. As detailed further below, mobile device 180 and server computer 106 may, in different embodiments, either together or individually, process waist measurement communications from belt 100 to create estimated waist measurements from tension and position measurements taken together by belt 100. These estimated waist measurements may then be aggregated and presented to the user either via mobile device 180 or via any other device of the user that is in communication with either mobile device 180 or server computer 106 via network 104.

FIG. 1C illustrates additional aspects of the belt 100 according to some example embodiments. As illustrated by FIG. 1C, belt buckle frame 110 of belt 100 includes a first belt attachment 112, a second belt attachment 114, a position measuring module 150, a tension measuring module 160, a memory device 175, and a wireless communication module 170.

The first end 121 of belt strap 120 is attached to the first belt attachment 112. The connection between the first end 121 of belt strap 120 and the first belt attachment 112 may be any fixed or adjustable connection. The second end 123 of belt strap 120 is attached to the second belt attachment 114 using attachment area 126. In various embodiments, the attachment of the first end 121 to the first belt attachment 112 and the attachment of the second end 123 to the second belt attachment 114 may both be adjustable, or only one of these connections may be adjustable. In FIG. 1C, only the attachment from a second end 123 to the second belt attachment 114 using attachment area 126 is shown as adjustable.

Position measuring module 150 is used to determine the attachment position of the second end 123 to the second belt attachment 114. Position measuring module 150 may use a number of different means to determine which attachment area of the attachment areas, including attachment area 126, attachment area 124, or attachment area 122, is attached to the second belt attachment 114. In one embodiment, position measuring module 150 may include a contact sensor in certain embodiments that senses patterns within the plurality of attachment areas 122 through 126. Such patterns may be variations in color, texture, or engraved patterns in a surface of at least a portion of an attachment area. For the illustrated attachment position at attachment area 126, position measuring module 150 may determine a position in belt strap 120 where the attachment between the second belt attachment 114 and the second end 123 occurs based both on the detected pattern from attachment area 126 and previously received belt information. The belt information describes the position of attachment area 126 within the belt strap 120. Given the position of attachment area 126 within the belt strap 120, a perimeter distance around the loop of the belt 100 and a user's waist may be determined.

In alternate embodiments, rather than a plurality of attachment areas 122, 124, and 126, an attachment position between second end 123 and second belt attachment 114 may occur at any portion along the belt strap 120. In such embodiments, different position measuring mechanisms may be used to determine the attachment position. For example, the position measuring mechanism may include a plurality of magnets with an arranged pattern that differentiates the magnetic field along the length of the second end 123. In such embodiments, position measuring module 150 may include a sensor to detect the variation in the magnetic field, and may determine the attachment position between the second end 123 and second belt attachment 114 based on the detected magnetic field.

In further embodiments, various circuits may be used to detect the attachment position. For example, various positions along second end 123 and different attachment areas along second end 123 may have differing resistance values associated with them. The circuit in position measuring module 150 may detect a particular resistance value at a certain attachment area and use this resistance value to determine a position where the second end 123 is attached the second belt attachment 114.

In still further embodiments, a pattern such as a color pattern may be unique in various attachment areas along a second end 123 of the belt strap 120. Position measuring module 150 may include a sensor to detect the patterns and to determine a position of attachment based on the pattern at the detected attachment area.

In various different embodiments where the position of attachment is detected, information associating a particular position with a perimeter distance may be stored in memory device 175. For example, in the embodiment of belt 100 shown by FIG. 1C, memory device 175 may store a distance from first belt attachment 112 to second belt attachment 114. The memory device 175 also stores a distance from the first belt attachment 112 along belt strap 120 to each of the plurality of attachment areas 122, 124, and 126. When the attachment area 126 is detected as a position of attachment between the second end 123 of belt strap 120 and the second belt attachment 114, the detected position may be used with the belt information in memory device 175 to determine a perimeter distance around belt 100.

Belt buckle frame 110 also includes tension measuring module 160. Tension measuring module 160 may include a number of different means for detecting tension in belt strap 120. For example, in one embodiment, tension measuring module 160 may include a spring with an attached electronic circuit that measures a tensile force exerted on both ends of the spring. The spring may be coupled between the first belt attachment 112 and the first end 121 of belt strap 120 such that the tensile force exerted on one end by belt strap 120 and on the other end by belt buckle frame 110 is transmitted through the spring. The tensile force measured by the circuit attached to the spring will thus be equal to the tension in belt strap 120. In alternate embodiments, a tension measuring module 160 may be disposed in the belt strap 120 rather than belt buckle frame 110.

In various embodiments, a tension measuring module may be any system or device for tension measurement. For example, a strain gauge may be used for tension measurements. In another example embodiment, such a tension measuring module 160 may include a first rigid frame with a first belt strap opening and the second belt strap opening. The first belt strap opening and the second belt strap opening each surround a separate section of the belt strap 120. A displacement point attachment may be coupled to the belt strap 120 at a point midway between the first belt strap opening and the second belt strap opening. The displacement point attachment may then be coupled to the rigid enclosure by a measurement element. During a tension measurement, the measurement element may apply a force perpendicular in any direction to the line of the belt strap 120. The distance of the displacement of the displacement point created by the application of the force perpendicular to the belt strap 120 may be used to calculate a tension in the belt strap 120. Alternatively, the force applied perpendicular to the line of the belt strap 120 may be generated such that a particular displacement distance perpendicular to the line of the belt strap 120 may be generated. The amount of force used may be used to calculate a tension in the belt strap 120.

Tension measurements and position measurements are taken as pairs such that each tension measurement will have an associated position measurement. Because, in certain embodiments, belt 100 and belt strap 120 may not perfectly encircle the user's waist with a given attachment position at an attachment area such as attachment area 126, the tension in belt strap 120 may not vary as a user's waist size changes. Tension measurement and the corresponding position measurement together may thus be used to generate a more accurate estimate of a user's waist size. In one embodiment, a particular belt may have an associated table that provides an estimated waist size for a corresponding pair of position measurements and tension measurements. If tension and/or position measurements do not exactly match the numbers in the table, values may be rounded up or down, or an interpolation may be used to further estimate a waist size based on the position and tension measurements. In other embodiments, rather than using a table to generate an estimated size, a formula may be used that estimates the waist size as a function of the position measurement that provides a circumference of the belt plus a tension adjustments to that:

[estimated waist size]=$f1$(position measurement)+$g1$(tension measurement)

Different belts may use different functions based on the qualities of the belt so that any number of different functions f1, f2, fn, and so on may be used with the position measurement and any number of different functions or weighting values g1, g2, gn, and so on may be used with tension measurements.

Tension measurement and a position measurement together may comprise a single waist measurement. Waist measurements may then be communicated to a separate remote device via wireless communication module 170. In various embodiments, a plurality of waist measurements may be stored in memory device 175 and then communicated via wireless communication module 170 as a set. In other embodiments, each individual pair of tension and position measurements may be communicated via wireless communication module 170 in a stream as the measurements are taken. In such embodiments, memory device 175 may merely be a temporary memory of either tension measuring module 160, position measuring module 150, or both. In embodiments where waist measurements are stored or aggregated at the belt 100, memory device 175 may be a separate nonvolatile memory device.

FIG. 2 illustrates a method 200 of waist measurement using a waist measuring belt according to some example embodiments. While method 200 may be used with a variety of different implementations of a waist measuring belt, method 200 is described below in the context of the particular example embodiment of belt 100.

Method 200 begins at operation 210 with measuring, using a tension measuring module 160, a first tension in a belt strap 120, wherein the belt strap 120, a belt buckle frame 110, and the tension measuring module 160 are all coupled as part of a belt 100. Additionally, the first tension is measured during a first time period. In various embodiments, the tension measuring module 160 may include electronic circuits for tension measurement, spring elements, or microelectronic machine elements, as well as memory storage or cache and associated electronic processing and/or filtering circuitry.

Operation 220 involves measuring, using a position measuring module 150 coupled to the belt 100, a first position where the belt strap 120 connects to the belt buckle frame 110. This measurement occurs during the first time period, and the first time period is such that the measurement of the first tension is reasonably associated with the measurement of the first position. This enables later waist size estimates to use both the first tension measurement and the first position measurement with the assumption that the perimeter enclosed by the belt 100 at the time of the first tension measurement may be determined from the first position measurement. In various embodiments, the position measuring module 150 may include measuring circuitry as well as mechanical measuring elements. Position measuring module 150 may also include memory storage or cache and associated electronic processing and/or filtering circuitry. In certain embodiments, position measuring module 150 may share memory, processing, or filtering elements with tension measuring module 160 or any other module that is integrated with belt 100.

Operation 230 involves measuring, using the tension measuring module 160, a second tension in the belt strap 120 during a second time period that is different from the first time period. Similar to the first time period, the second time period need only be reasonably allocated such that a second position may be reasonably associated with the second tension. Additionally, the second time period is different from the first time period to the extent that the waist measurements generated using the position measurements and the tension measurements are used to estimate a waist size over time. In certain embodiments, waist measurements comprising a tension measurement and an associated position measurement may be taken at predetermined intervals. Such an interval may be once a minute or once an hour. This data may be aggregated for later use in estimating a waist size using a table or function as described above, or may be used immediately to estimate a waist size for each position/tension pair, with the estimated waist sizes stored, or both.

In addition to measurement of waist size, such waist measurements may, in certain embodiments, be used to measure additional details associated with a user. For example, in certain embodiments, a sufficiently sensitive tension measuring module 160 may detect a user's heartbeat under appropriate conditions. In an implementation configured to detect a user's heart rate, the tension measuring module 160 may perform multiple measurements per second. All of this information may be stored, or in certain embodiments, filtering circuitry may be used to determine when noise in the measurements overwhelms the target information from the sensor. Such noise may be from user movement, background vibration from a vehicle, or other such sources. Such filtering circuitry may be used to remove data with undesired noise, and retain only information without such background noise, where the target information is available from the waist measurements. In still further embodiments, a separate heart rate measurement module separate from the tension measuring module 160 may be present and used to gather heart rate information. In such embodiments, this information may be aggregated with waist measurements for communication purposes.

Operation 240 involves measuring, using the position measuring module 150, a second position where the belt strap 120 connects to the belt buckle frame 110 during the second time period. In certain embodiments, the second position may be determined to be equal to the first position by determining that an attachment position has not changed since the first time period.

Operation 250 involves communicating, using a wireless communication module 170 coupled to the belt buckle frame 110, the first tension, the second tension, the first position, and the second position to a first device such as mobile device 180. As mentioned above, the tension and position measurements may be stored locally in memory and aggregated to be sent as a set to a remote device such as mobile device 180. In other embodiments, operation 250 may occur as each measurement is taken, such that pairs of tension and position measurements are streamed from belt 100 as the measurements occur.

Figure 3:
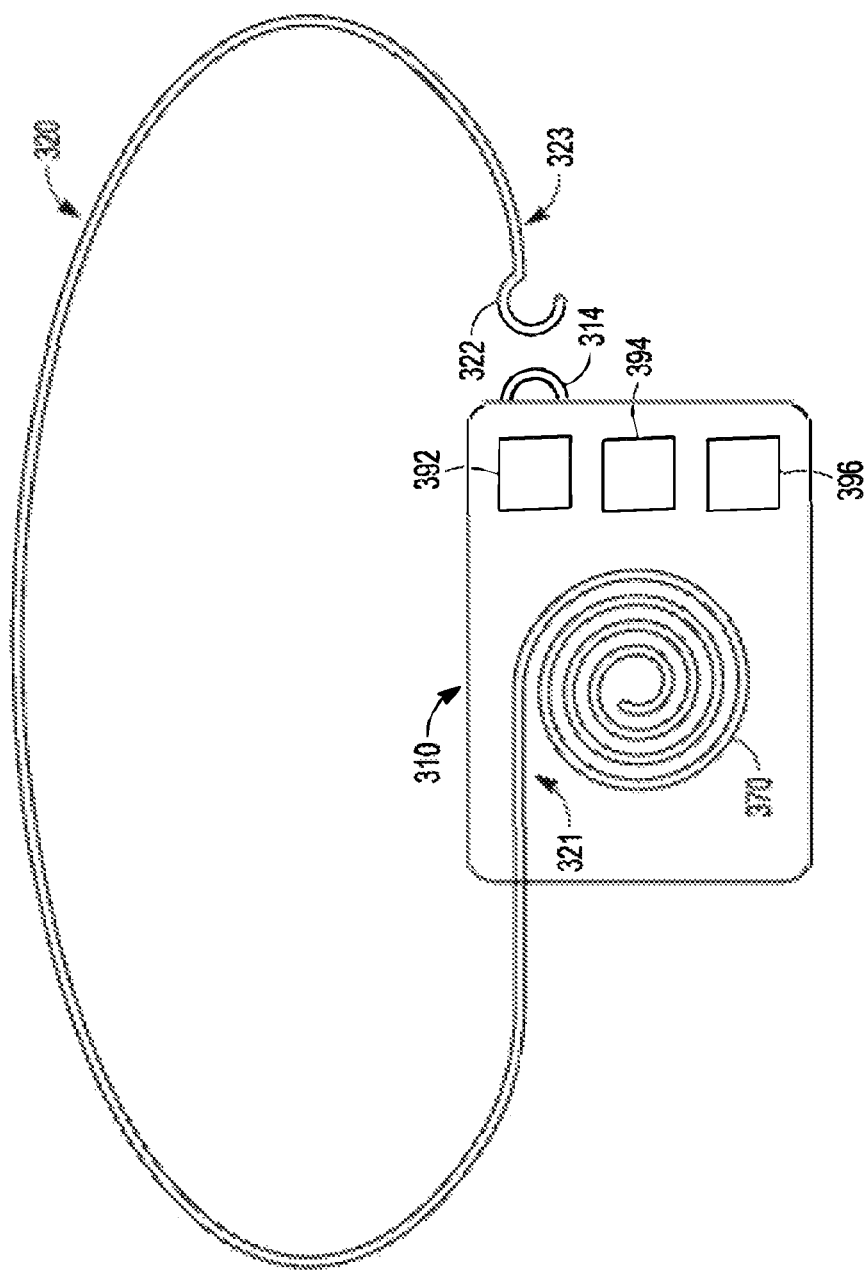
FIG. 3 illustrates another waist measuring belt, according to some example embodiments.

FIG. 3 illustrates another belt 300 for waist measurement according to some example embodiments. Belt 300 includes belt buckle frame 310 and belt strap 320. Belt strap 320 has a first end 321 and a second end 323 as well as an attachment area 322. In belt 300, attachment area 322 of belt strap 320 attaches to belt buckle frame 310 at second belt attachment 214. In contrast to belt 100, belt 300 includes a belt strap 320 with a single attachment area 322. Belt 300, however, includes a belt strap coil 370 which is stored within belt buckle frame 310.

In belt 300, belt strap coil 370 may be used both to measure a position and to measure a tension within belt strap 320. Belt strap coil 370 may include a spring or other tension source to exert a continuous force on the first end 321 of belt strap 320. If the second end 323 of belt strap 320 is not attached to second belt attachment 214 or another fixed position, then the force exerted by belt strap coil 370 on the first end 321 will result in belt strap 320 being retracted into belt buckle frame 310 as part of belt strap coil 370. If the second end 323 is connected to second belt attachment 314 via attachment area 322, then the user's waist and the second belt attachment 314 along with belt strap coil 370 will keep belt strap 320 in place. As the user's waist size changes, belt strap coil 370 will wind and unwind to compensate for changes in the user's waist size. Additionally, tension in belt strap 320 may be measured by the amount of force placed on belt strap coil 370. Belt strap coil 370 may have a tension force window. Inside the window, the coil will not move. Outside the window, the belt strap coil 370 will rotate. Tension values within the window may be measured as part of a tension measuring module. Tension values above this rotation window will cause the belt strap 320 to extend from belt buckle frame 310 and belt strap coil 370 to unwind. Tension values below this rotation window will cause the belt strap 320 to retract and be gathered into belt strap coil 370. In the embodiment of belt 300, belt strap coil 370 acts as a first belt attachment as well as at least a portion of a tension measuring module and a position measuring module. In certain embodiments, a tension measurement may be taken once as an initial calibration, with a sensor to detect changes in tension rather than re-measuring tension for each position measurement. In such an embodiment, a tension/position pair may be generated using a previous tension measurement without a new tension measurement for each tension/position data pair that is used for a waist size estimate.

One or more processors 394 may be used with belt strap coil 370 and additional measurement circuits or other elements to create measurement data. A position may be determined from a rotation position of belt strap coil 370. Tension may be determined from a tension measurement associated with a rotational force on belt strap coil 370. The position and tension measurements derived from belt strap coil 370 may generate measurements which are stored in memory 392. Wireless input/output (I/O) 396 may then be used to communicate these waist measurements to remote devices such as a mobile device 180 or a server computer 106.

In various embodiments, belt 300 may be structured to be attached to other belt elements. For example, belt strap 320 may be a thin string or chain which may be attached to a larger, more traditional belt strap. Similarly, belt buckle frame 310 may be a small encapsulated structure which contains the memory 392, one or more processors 394, wireless I/O 396, and belt strap coil 370 as well as any other associated position measuring module and tension measuring module elements. A larger belt buckle front may be attached to belt buckle frame 310 to match the traditional belt strap. Belt 300 may thus be a modular belt with elements illustrated by FIG. 3. The belt strap 320 and belt buckle frame 310 of such an embodiment are functional elements that are covered by other interchangeable coverings. Alternatively, belt 300 may be designed to be worn inside of a user's clothes with a separate belt over the clothes which is not integrated with belt 300. In such an embodiment, belt strap 320 may comprise a thin line of string, a thin chain, or other material that may be compactly structured when wound as part of belt strap coil 370. In such an embodiment, belt buckle frame 310 may include an outer covering with flat top and bottom surfaces. The flat bottom surface may be structured to lie flat against a user's skin, with the flat top surface designed to protect the internal elements of belt buckle frame 310 from a user's clothing or other external contact.

Figure 4:
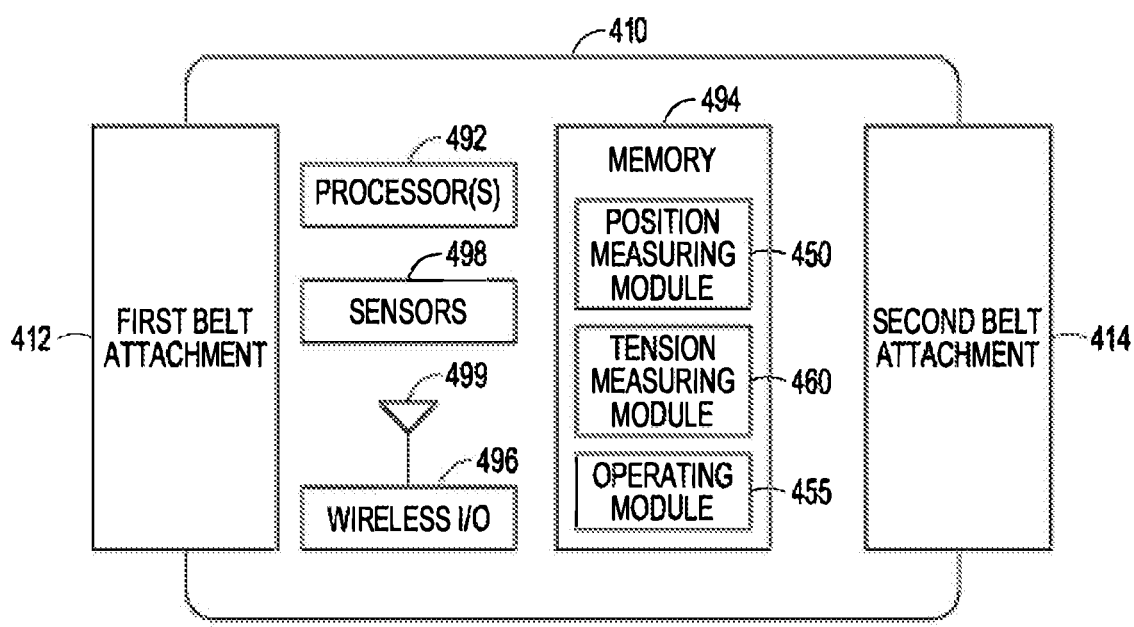
FIG. 4 illustrates a belt buckle frame for a waist measuring belt, according to some example embodiments.

FIG. 4 illustrates a belt buckle frame 410 for a waist measuring belt according to some example embodiments. The belt buckle frame 410 is not shown with a particular associated belt strap. As described above, certain embodiments may modularly be associated with multiple different elements such as multiple different belt straps. Belt buckle frame 410 does include a first belt attachment 412 and a second belt attachment 414. At least one of the belt attachments 412 and 414 will include an adjustable interface for attaching to a belt strap. Belt buckle frame 410 additionally includes one or more processors 492, one or more sensors 498, wireless input/output (I/O) 496, an antenna 499 coupled to the wireless I/O 496, and memory 494. Memory 494 includes processor readable instructions that when used with one or more processors 492 may be used as at least part of a position measuring module 450, a tension measuring module 460, and one or more operating modules 455. These modules may operate with processors 492 and sensors 498 to gather position and tension measurements and to communicate measured position and tension values to other devices via wireless I/O 496 and antenna 499.

Additionally, because there is no particular belt strap associated with belt buckle frame 410, memory 494 may also receive and store belt strap information that may be used by position measuring module 450 and tension measuring module 460. For example, when a particular belt strap is attached to the belt buckle frame 410 via first belt attachment 412 and second belt attachment 414, belt strap information associated with this particular belt strap may be communicated to memory 494 via wireless I/O 496. This may include length information, information associated with various attachment areas of the belt strap, and flexibility information which may be used to determine how a particular tension measurement may be used to estimate a user's waist size. For example, this belt strap information may include a flexibility value. The flexibility value may identify that a high tension value on a flexible belt may significantly alter a waist size estimate from an expected perimeter that is only based on an attachment position of the belt strap to the second belt attachment 414 and the first belt attachment 412. The belt strap information may additionally include any other information associated with aspects of the belt strap that will impact a determination of a belt perimeter when a belt is attached in a particular configuration, and information that will relate a measured tension in the belt strap with an estimated user waist size.

As different belt straps are attached to the belt buckle frame 410, new belt strap information associated with the newly attached belt strap may be communicated to memory 494 via wireless I/O 496. This new information may then be used for waist measurements taken while the new belt strap is attached to the belt buckle frame 410. As waist measurements are taken and stored in memory 494, the waist measurements may be communicated to other devices along with belt strap information. This belt strap information may be used by the other devices to estimate the user's waist size using not only the position and tension measurements but also the belt strap information that may be used to interpret these measurements. This may enable a remote device such as mobile device 180 or server computer 106 to generate standardized estimated waist sizes even when measurements are taken using different belt straps, belts, belt buckle frames, or other elements of multiple different implementations of a waist measuring belt described herein.

Figure 5:
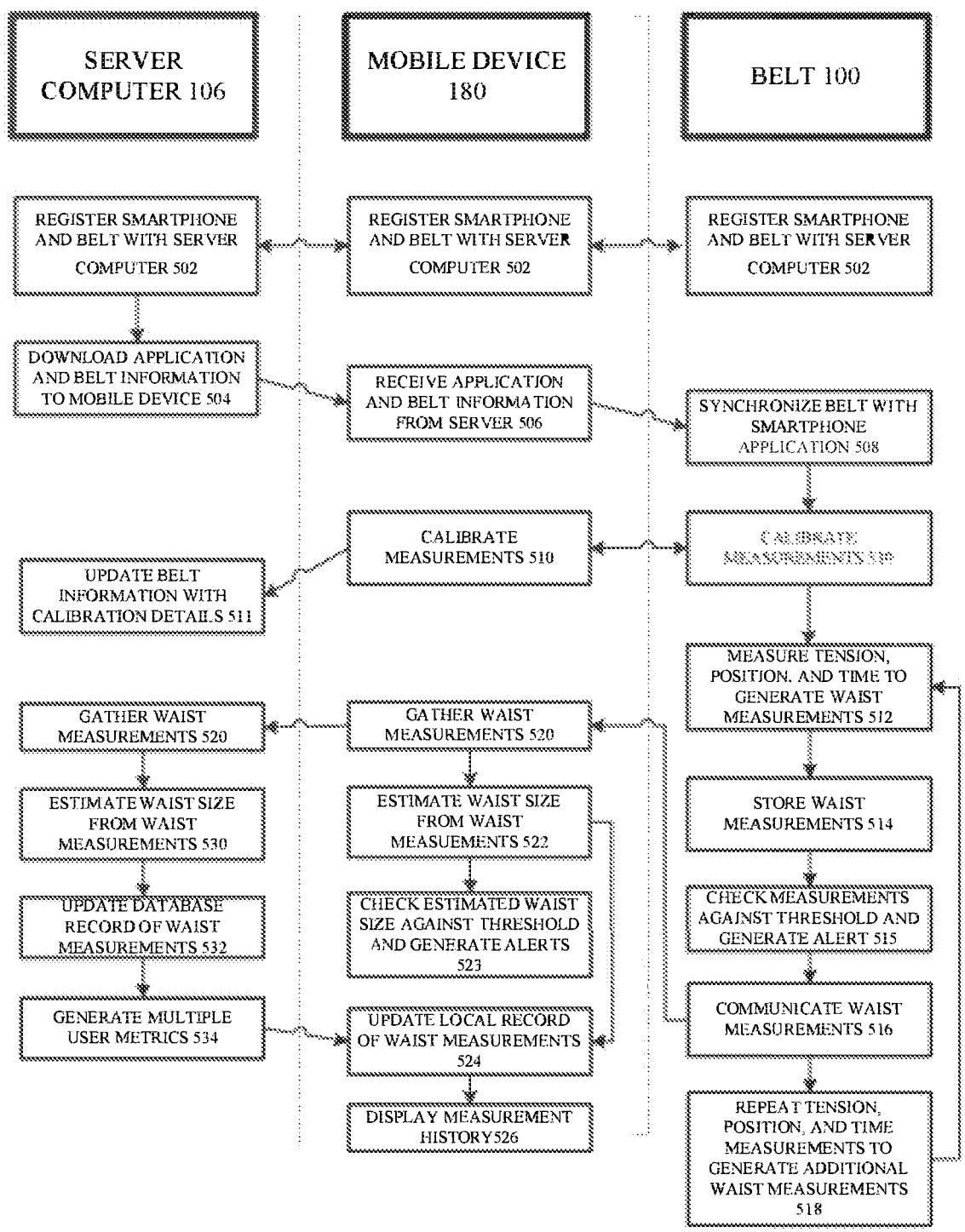
FIG. 5 is a flow diagram illustrating aspects of waist measurement using a waist measuring belt, according to some example embodiments.

FIG. 5 is a flow diagram illustrating aspects of a method 500 of waist measurement using a waist measuring belt according to some example embodiments. While the method 500 may be used with a variety of different embodiments of a waist measuring belt, including both embodiments described herein as well as other embodiments not specifically described herein that operate in accordance with the described innovations, the method 500 will be described with respect to system 101 for illustrative purposes.

Method 500 illustrates operations by server computer 106, mobile device 180, and belt 100. Method 500 additionally illustrates communications between these elements. Method 500 begins with operation 502, in which any mobile device 180 or belt 100 associated with the user may be registered with server computer 106. In various embodiments, this may involve multiple mobile devices 180 and multiple belts 100 being registered with server computer 106. Such a registration may be accomplished a number of different ways. In certain embodiments, a separate computing device of a user may be used to contact server computer 106 via a network such as network 904. The user may provide identifying details for mobile device 180 and belts 100 to server computer 106. The user may additionally generate a login and password or other security information that enables mobile device 180 to communicate with server computer 106 securely and a store information such as the user's measurements and estimated waist size at server computer 106 or a storage device associated with server computer 106. In embodiments with modular belts, multiple belt straps may be associated with different belt buckle frames, and calibration information for position and force measurements made with each combination of belt strap and belt buckle frame may be associated with the user's account by server computer 106.

After the user registers with server computer 106, in operation 504 server computer 106 provides an application and belt information to mobile device 180. In operation 506, the mobile device 180 receives the application and belt information from server computer 106. The application may include instructions readable by a processor of mobile device 180 in order to retrieve measurement information from belt 100, estimate a user's waist size using measurements from belt 100, communicate with server computer 106 to receive additional information associated with the user's waist measurements such as anonymized waist measurements for other similar users, and any other operation enabled by a system in conjunction with belt 100.

In operation 508, belt 100 synchronizes with mobile device 180 to enable belts 100 to communicate position and tension measurements from belt 100 to mobile device 180. This synchronizing operation of operation 508 may include handshaking operations as part of any communication protocol described below.

Operation 510 involves calibration for measurements taken by belt 100. In certain embodiments, this calibration may simply involve identification of a belt buckle frame 110 and belt strap 120 which are part of belt 100. This may enable mobile device 180 to identify belt information received from server computer 106. Mobile device 180 may then use this belt information to interpret measurement values received from belt 100. In other embodiments, particular measurements may be taken as part of operation 510. For example, a user may be asked to perform a specific measurement of both tension and position to verify the correctness of belt information received from server computer 106. Such a calibration process may involve independent measurements of belt length from a belt tip to the attachment area using an independent measurement device such as a ruler. This may also involve hanging a weight from one end of a belt and communicating the resulting tension measurement from a tension measuring module 160 of belt 100 to mobile device 180. This may also involve any other similar calibration measurement related to position and tension measurements that may be taken by belt 100. In certain embodiments, a belt buckle that is attached to the belt buckle frame or the belt buckle frame itself may act as this weight.

When such calibration measurements are performed, resulting data may be communicated to server computer 106 in operation 511. In operation 511, server computer 106 may receive calibration measurements from mobile device 180, and may use this information to update belt information stored at server computer 106. For example, server computer 106 may include a database of calibration measurements taken by users in association with particular belt types. Each belt type may have an associated history of calibration measurements taken by a large number of users. This crowdsourced calibration measurement information may be used to update and generate belt information over time. This updated belt information may then be communicated to system users during registration, or other update communications from server computer 106 to mobile device 180 and any other device in the system.

Following a calibration process, in operation 512, belt 100 may measure tension, position, and time to generate waist measurements. These tension and position measurements along with information about the time at which the measurements were taken may be stored in a memory of belt 100 in operation 514.

In certain embodiments, a belt 100 may include a set of thresholds. The thresholds may be provided by the user during the calibration or registration process. In other embodiments, a threshold may be a default system value which may be adjusted by a user. In operation 515, waist measurements stored in operation 514 may be checked against one or more threshold values. Such a threshold may be set by a user as an assistance for weight loss. If a threshold is exceeded, an alert may be generated to alert the user that the threshold has been exceeded. The alert may involve a vibration or sound generated by belt 100, and the alert may also include a communication sent to another device such as mobile device 180 via a wireless communication interface of belt 100.

In operation 516, waist measurements stored at belt 100 may be communicated to mobile device 180. In operation 518, the process of measuring, storing measurement values, checking for measurements that exceed threshold values, and communicating waist measurements may be repeated. This repetition may be periodic or based on some trigger. In certain embodiments, the various elements may be repeated at different frequencies than are various other elements. For example, in certain embodiments, waist measurements may be communicated daily even though waist measurement values may be generated multiple times per second, minute, or hour.

In operation 520, mobile device 180 receives waist measurements from belt 100. In operation 522, mobile device 180 uses tension and position measurements received from belt 100 to generate an estimated waist size. As described above, this may be done using a table of information that is stored locally at a belt or that is stored remotely at a mobile device or server computer. This waist estimate may include weighted calculations using belt information, calibration information, position information, tension information, user profile information, and any other such information which may be used to estimate a user's waist size using any method including the table or formula methods mentioned above. For example, in one embodiment, a belt perimeter is calculated using belt information and a position measurement from belt 100. A tension measurement may then be used with additional belt information about the flexibility of a belt strap 120 that is part of belt 100, in order to estimate a user's waist size based on a base waist size which is equal to the belt perimeter plus an adjustment value generated from the tension and the belt information. Additional details of various processes for estimating waist size from waist measurements are described below with respect to FIG. 6B.

In operation 523, threshold values stored in mobile device 180 may be checked against estimated waist sizes generated at operation 522. If a threshold is exceeded, mobile device 180 may generate an alert. This may involve communication to a user account such as an email, phone, or other such account. In certain embodiments, this may involve a wireless communication to belt 100 which initiates a vibration or sound at a transceiver of belt 100. In certain embodiments, operation 515 and operation 523 may work together to generate alerts to a user.

In operation 520, waist measurements from belt 100 may be communicated not only to mobile device 180, but also to server computer 106. A determination of whether information will be communicated to mobile device 180, server computer 106, or both may be set by a structure of system 101, a user selection as part of a registration process, or some other system input. For embodiments where waist measurements are gathered by server computer 106, the server computer 106 may estimate waist size from the waist measurements in operation 530 just as described with regard to operation 522.

In operation 532, a database record of waist measurements is updated using the waist measurement values and waist size estimates from operations 520 and 530. In certain embodiments, this information may then additionally be used to generate multiple user metrics in operation 534. Such metrics may use measurements and estimates not only from a user of belt 100, but also from users of other belts. This may include multiple belts worn by a single user, a single belt style worn by multiple users, multiple different belts worn by multiple different users, or any other such combination of waist measurement values, estimated waist sizes, or any other such system information. The multiple user metrics of operation 534 may enable a registered user to compare the user's waist measurements with the measurements of other users. Information from multiple different users may be stripped of identifying information and provided as statistical information. As part of this process, in operation 534 information from the user of belt 100 may be aggregated with information of other users into statistical values which make up system metrics.

In operation 524, waist measurement values, estimated waist size values, and any metrics from server computer 106 may be received by mobile device 180 and used to update a local record. This local record may then be used in operation 526 to generate a measurement history display. An example measurement history display is illustrated by FIG. 6B.

Figure 6A:
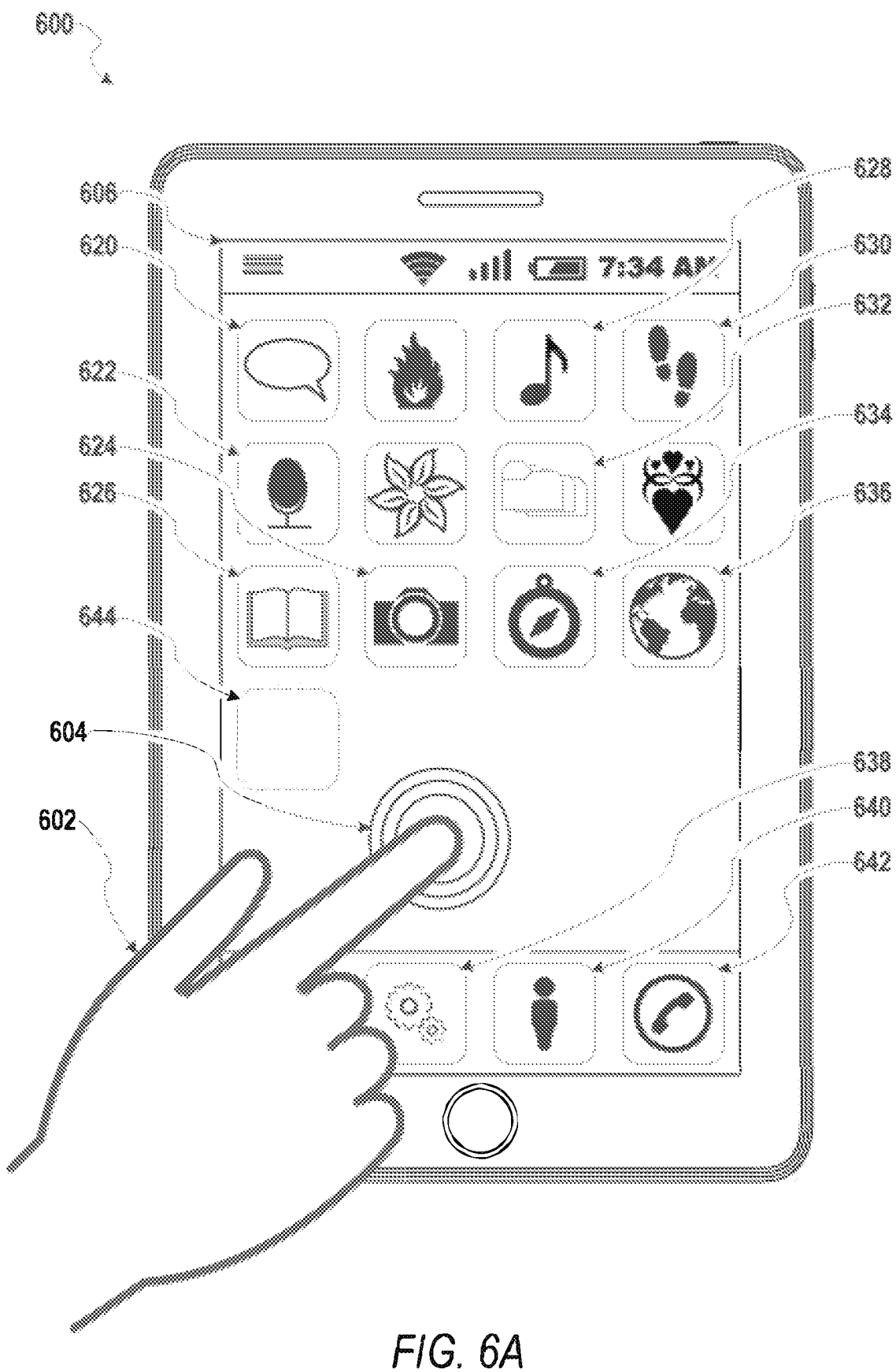
FIG. 6A depicts an example mobile device and mobile operating system interface, according to some example embodiments.
Figure 6B:
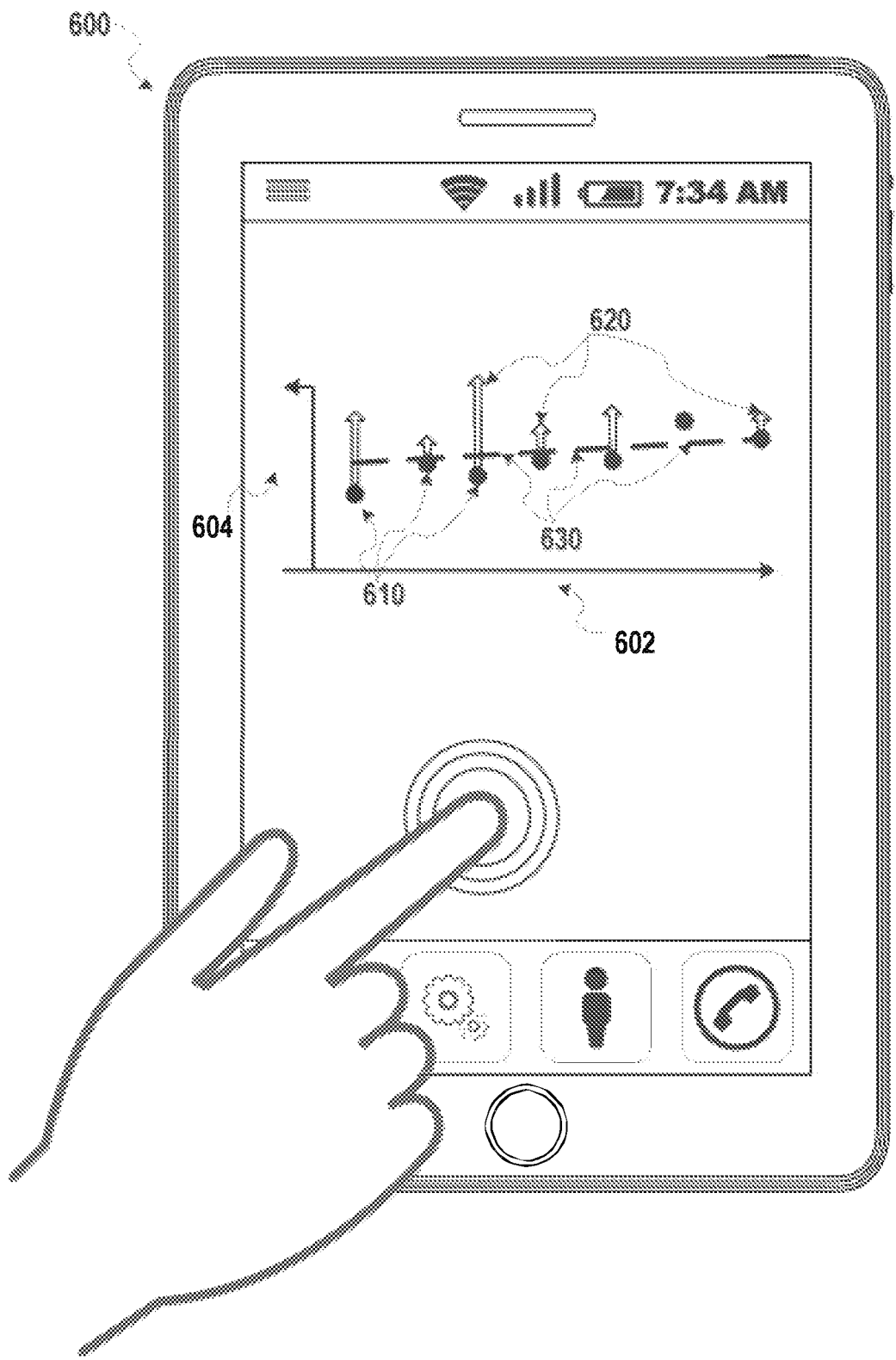
FIG. 6B depicts an example mobile device and mobile operating system interface, according to some example embodiments.

FIGS. 6A and 6B depict an example mobile device and mobile operating system interface, according to some example embodiments. FIG. 6A illustrates an example mobile device 600 that may be executing a mobile operating system (e.g., iOS™, Android™, Windows® Phone, or other mobile operating systems), according to example embodiments. In certain embodiments, mobile device 180 may be implemented as mobile device 600. In one embodiment, the mobile device 600 may include a touch screen that may receive tactile information from a user 602. For instance, the user 602 may physically touch 604 the mobile device 600, and in response to the touch 604, the mobile device 600 may determine tactile information such as touch location, touch force, gesture motion, and so forth. In various example embodiments, the mobile device 600 may display home screen 606 (e.g., Springboard on iOS™) that the user 602 of the mobile device 600 may use to launch applications and otherwise manage the mobile device 600. In various example embodiments, the home screen 606 may provide status information such as battery life, connectivity, or other hardware status. The home screen 606 may also include a plurality of icons that may be activated to launch applications, for example, by touching 604 the area occupied by the icon. Similarly, other user interface elements may be activated by touching 604 an area occupied by a particular user interface element. In this manner, the user 602 may interact with the applications.

Many varieties of applications (also referred to as "apps") may be executing on the mobile device 600. The applications may include native applications (e.g., applications programmed in Objective-C running on iOS™ or applications programmed in Java running on Android™), mobile web applications (e.g., HTML5), or hybrid applications (e.g., a native shell application that launches an HTML5 session). In a specific example, the mobile device 600 may include a messaging app 620, audio recording app 622, a camera app 624, a book reader app 626, a media app 628, a fitness app 630, a file management app 632, a location app 634, a browser app 636, a settings app 638, a contacts app 640, a telephone call app 642, other apps (e.g., gaming apps, social networking apps, biometric monitoring apps), a third party app 644, and so forth.

A fitness app 630 may, in certain embodiments, be an application downloaded to a mobile device 180 from a server computer 106 as part of operations 504 and 506 described above. Fitness app 630 may manage calibration and measurement communication between a mobile device 600 and a belt or belt buckle frame such as belt 100, belt 300, or belt buckle frame 410. Fitness app 630 may receive tension and position measurements from a waist measuring belt, use this information along with belt information to generate estimated waist sizes, and standardize estimated waist sizes generated from different configurations of waist measuring belts with different belt straps or belt buckle frames.

FIG. 6B illustrates a display of waist measurements and estimated waist sizes that may be equivalent to the display generated in operation 526. This includes time scale 652, measurement scale(s) 654, position values 660, tension values 670, and estimated waist values 680. In certain embodiments, time scale 652 may, for example, illustrate measurements taken over the course of a single day. This may track a user's waist size during consumption of a large meal, for example. In other embodiments time scale 652 may track multiple days, months, or years. Measurement scales 654 may include values for tracking position, force, and estimated waist size, or may include only a scale for estimated waist size. Position values 660 may be direct values received from belt 100, or may be perimeter values calculated from attachment positions detected by belt 100 using a position measuring module 150. Tension values 670 may similarly be direct values, or may be values processed using calibration parameters. In certain embodiments, an output display as shown by FIG. 6B may include data from multiple belts which are standardized using belt information or calibration parameters to standardize the values across measurements from different belt devices. Estimated waist size values 680 are values calculated using the position values 660 and tension values 670. For example, when tension values are high, an estimated waist size value differs from the position value by a larger amount than when a tension value is low, as illustrated by the tension arrows of tension values 670 reflecting a larger tension magnitude. If a tension value is low or nonexistent, the associated position value may be ignored or averaged into other estimated waist size measurements, since a low tension may be associated with a belt perimeter that does not match a user's waist at all.

Figure 7:
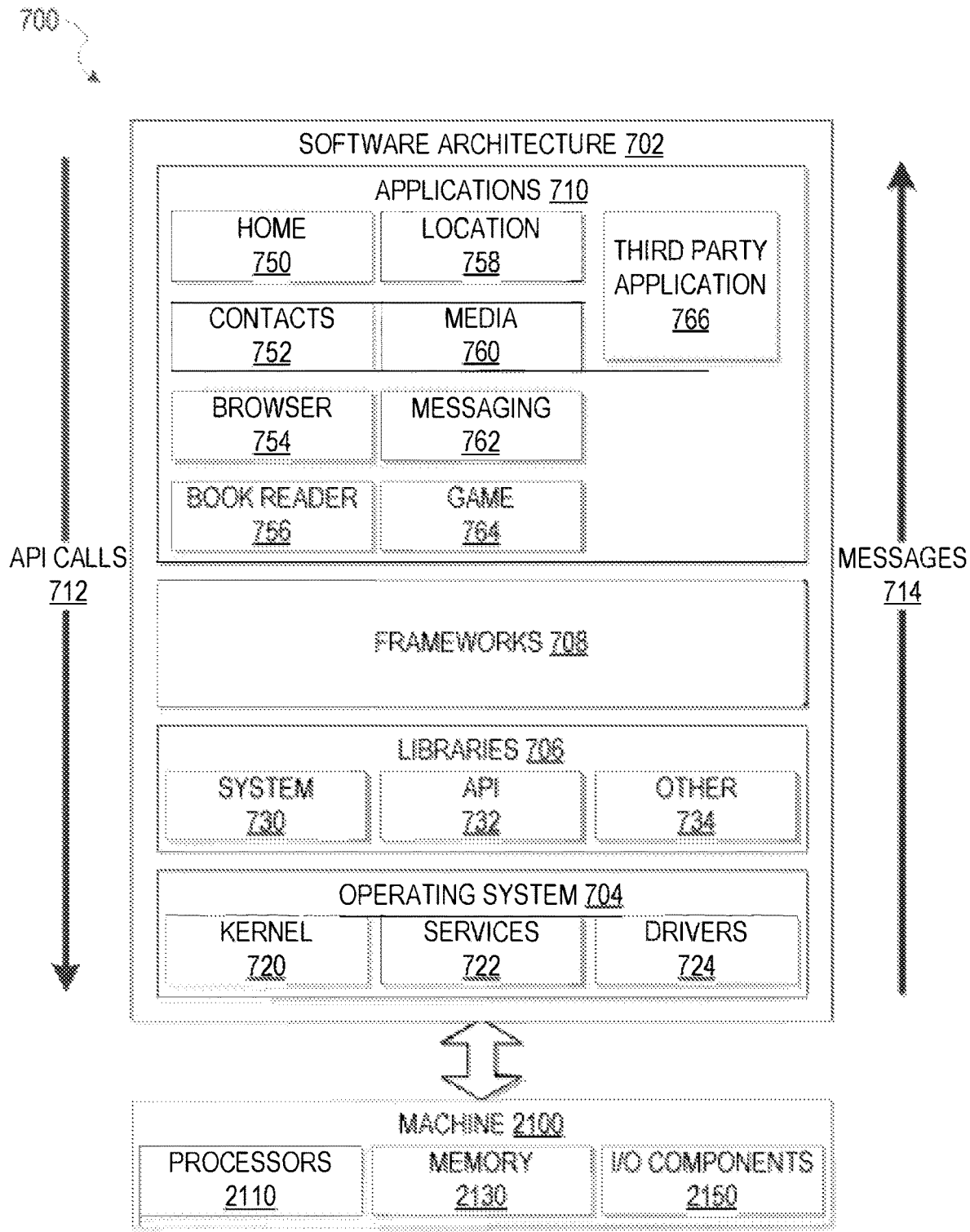
FIG. 7 is a block diagram illustrating an example of a software architecture that may be installed on a machine, according to some example embodiments.

FIG. 7 is a block diagram 700 illustrating an architecture of software 702 which may be installed on any one or more of the devices described herein, including mobile devices 180 and 600 which may operate a fitness application 630. FIG. 7 is merely a non-limiting example of a software architecture and it will be appreciated that many other architectures may be implemented to facilitate the functionality described herein. The software 702 may be executing on hardware such as machine 800 of FIG. 8 that includes processors 810, memory 830, and I/O components 850. In the example architecture of FIG. 7, the software 702 may be conceptualized as a stack of layers where each layer may provide particular functionality. For example, the software 702 may include layers such as an operating system 704, libraries 706, frameworks 708, and applications 710. Operationally, the applications 710 may invoke application programming interface (API) calls 712 through the software stack and receive messages 714 in response to the API calls 712.

The operating system 704 may manage hardware resources and provide common services. The operating system 704 may include, for example, a kernel 720, services 722, and drivers 724. The kernel 720 may act as an abstraction layer between the hardware and the other software layers. For example, the kernel 720 may be responsible for memory management, processor management (e.g., scheduling), component management, networking, security settings, and so on. The services 722 may provide other common services for the other software layers. The drivers 724 may be responsible for controlling or interfacing with the underlying hardware. For instance, the drivers 724 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth.

The libraries 706 may provide a low-level common infrastructure that may be utilized by the applications 710. The libraries 706 may include system libraries 730 (e.g., C standard library) that may provide functions such as memory allocation functions, string manipulation functions, mathematic functions, and the like. In addition, the libraries 706 may include API libraries 732 such as media libraries (e.g., libraries 706 to support presentation and manipulation of various media format such as MPEG4, H.264, MP3, AAC, AMR, JPG), graphics libraries (e.g., an OpenGL framework that may be used to render 2D and 3D in graphic content on a display), database libraries (e.g., SQLite that may provide various relational database functions), web libraries (e.g., WebKit that may provide web browsing functionality), and the like. The libraries 706 may also include a wide variety of other libraries 734 to provide many other APIs to the applications 710.

The frameworks 708 may provide a high-level common infrastructure that may be utilized by the applications 710. For example, the frameworks 708 may provide various graphic user interface (GUI) functions, high-level resource management, high-level location services, and so forth. The frameworks 708 may provide a broad spectrum of other APIs that may be utilized by the applications 710, some of which may be specific to a particular operating system or platform.

The applications 710 include a home application 750, a contacts application 752, a browser application 754, a book reader application 756, a location application 758, a media application 760, a messaging application 762, a game application 764, and a broad assortment of other applications 710 such as third party application 766. In a specific example, the third party application 766 (e.g., an application developed using the Android™ or iOS™ software development kit (SDK) by an entity other than the vendor of the particular platform) may be mobile software running on a mobile operating system 704 such as iOS™, Android™, Windows® Phone, or other mobile operating systems. In this example, the third party application 766 may invoke the API calls 712 provided by the operating system 704 to facilitate functionality described herein. In various embodiments, these applications may interact with a fitness application 630 in various ways. For example, a messaging application 762 may be used for alerts or any communications with a waist measuring belt. A game application 764 may receive estimated waist values or other waist measurements as inputs to a game over time that may present a user with achievements based on waist measurements in conjunction with exercise inputs, heart rate inputs, or other such inputs.

Figure 8:
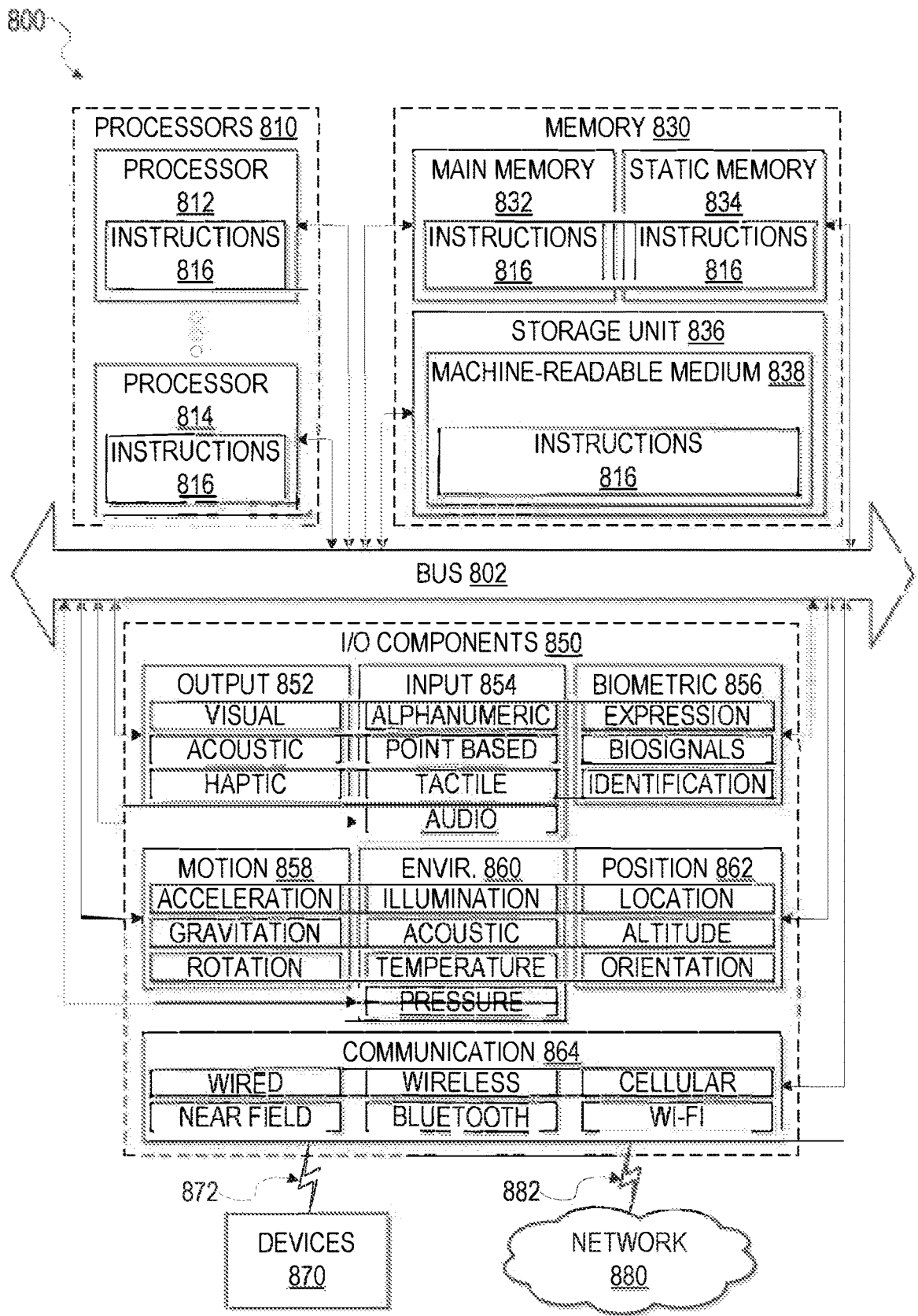
FIG. 8 illustrates a diagrammatic representation of a machine in the form of a computer system within which a set of instructions may be executed for causing the machine to perform any one or more of the methodologies discussed herein, according to an example embodiment.

FIG. 8 is a block diagram illustrating components of a machine 800, according to some example embodiments, able to read instructions from a machine-readable medium (e.g., a machine-readable storage medium) and perform any one or more of the methodologies discussed herein, including operation of a fitness application 630 that communicates with a waist measuring belt. Specifically, FIG. 8 shows a diagrammatic representation of the machine 800 in the example form of a computer system, within which instructions 816 (e.g., software, a program, an application, an applet, an app, or other executable code) for causing the machine 800 to perform any one or more of the methodologies discussed herein may be executed. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device 600, a wearable device (e.g., a smart watch), a smart home device (e.g., a smart appliance), other smart devices, a web appliance, a network router, a network switch, a network bridge, or any machine capable of executing the instructions 816, sequentially or otherwise, that specify actions to be taken by machine 800. Further, while only a single machine 800 is illustrated, the term "machine" shall also be taken to include a collection of machines 800 that individually or jointly execute the instructions 816 to perform any one or more of the methodologies discussed herein.

The machine 800 may include processors 810, memory 830, and I/O components 850, which may be configured to communicate with each other via a bus 802. In an example embodiment, the processors 810 (e.g., a central processing unit (CPU), a reduced instruction set computing (RISC) processor, a complex instruction set computing (CISC) processor, a graphics processing unit (GPU), a digital signal processor (DSP), an application specific integrated circuit (ASIC), a radio-frequency integrated circuit (RFIC), another processor, or any suitable combination thereof) may include, for example, a processor 812 and a processor 814 that may execute the instructions 816. The term "processor" is intended to include multi-core processor that may comprise two or more independent processors (also referred to as "cores") that may execute the instructions 816 contemporaneously. Although FIG. 8 shows multiple processors 810, the machine 800 may include a single processor 810 with a single core, a single processor 810 with multiple cores (e.g., a multi-core process), multiple processors 810 with a single core, multiple processors 810 with multiples cores, or any combination thereof.

The memory 830 may include a main memory 832, a static memory 834, and a storage unit 836 accessible to the processors 810 via the bus 802. The storage unit 836 may include a machine-readable medium 838 on which are stored the instructions 816 embodying any one or more of the methodologies or functions described herein. The instructions 816 may also reside, completely or at least partially, within the main memory 832, within the static memory 834, within at least one of the processors 810 (e.g., within the processor's cache memory), or any suitable combination thereof, during execution thereof by the machine 800. Accordingly, the main memory 832, static memory 834, and the processors 810 may be considered machine-readable media 838.

As used herein, the term "memory" refers to a machine-readable medium 838 able to store data temporarily or permanently and may be taken to include, but not be limited to, random-access memory (RAM), read-only memory (ROM), buffer memory, flash memory, and cache memory. While the machine-readable medium 838 is shown in an example embodiment to be a single medium, the term "machine-readable medium" should be taken to include a single medium or multiple media (e.g., a centralized or distributed database, or associated caches and servers) able to store instructions 816. The term "machine-readable medium" shall also be taken to include any medium, or combination of multiple media, that is capable of storing instructions (e.g., instructions 816) for execution by a machine (e.g., machine 800), such that the instructions 816, when executed by one or more processors of the machine 800 (e.g., processors 810), cause the machine 800 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory (e.g., flash memory), an optical medium, a magnetic medium, other non-volatile memory (e.g., erasable programmable read-only memory (EPROM)), or any suitable combination thereof. The term "machine-readable medium" specifically excludes non-statutory signals per se. Any such memory may be included as part of memory device 175, memory 392, memory 494, or any other memory of a belt 100, mobile device 180, server computer 106, or other computing device which communicates with a waist measuring belt as described herein.

The I/O components 850 may include a wide variety of components to receive input, provide output, produce output, transmit information, exchange information, capture measurements, and so on. It will be appreciated that the I/O components 850 may include many other components that are not shown in FIG. 8. The I/O components 850 are grouped according to functionality merely for simplifying the following discussion, and the grouping is in no way limiting. In various example embodiments, the I/O components 850 may include output components 852 and input components 854. The output components 852 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor), other signal generators, and so forth. The input components 854 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instruments), tactile input components (e.g., a physical button, a touch screen that provides location and force of touches or touch gestures, or other tactile input components), audio input components (e.g., a microphone), and the like.

In further example embodiments, the I/O components 850 may include biometric components 856, motion components 858, environmental components 860, or position components 862 among a wide array of other components. For example, the biometric components 856 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 858 may include acceleration sensor components (e.g., accelerometer), gravitation sensor components, rotation sensor components (e.g., gyroscope), and so forth. The environmental components 860 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment. The position components 862 may include location sensor components (e.g., a Global Positioning System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 850 may include communication components 864 operable to couple the machine 800 to a network 880 or devices 870 via coupling 882 and coupling 872 respectively. For example, the communication components 864 may include a network interface component or other suitable device to interface with the network 880. In further examples, communication components 864 may include wired communication components, wireless communication components, cellular communication components, near field communication (NFC) components, Bluetooth® components (e.g., Bluetooth® Low Energy), Wi-Fi® components, and other communication components 864 to provide communication via other modalities. The devices 870 may be another machine 800 or any of a wide variety of peripheral devices (e.g., a peripheral device coupled via a Universal Serial Bus (USB)).

Moreover, the communication components 864 may detect identifiers or include components operable to detect identifiers. For example, the communication components 864 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) codes, Aztec code, Data Matrix, Dataglyph, MaxiCode, PDF417, Ultra Code, UCC RSS-2D bar codes, and other optical codes), or acoustic detection components (e.g., microphones to identify tagged audio signals). In addition, a variety of information may be derived via the communication components 864, such as location via Internet Protocol (IP) geo-location, location via Wi-Fi® signal triangulation, location via detecting an NFC beacon signal that may indicate a particular location, and so forth.

The instructions 816 may be transmitted or received over the network 880 using a transmission medium via a network interface device (e.g., a network interface component included in the communication components 864) and utilizing any one of a number of well-known transfer protocols (e.g., hypertext transfer protocol (HTTP)). Similarly, the instructions 816 may be transmitted or received using a transmission medium via the coupling 872 (e.g., a peer-to-peer coupling) to devices 870. The term "transmission medium" shall be taken to include any intangible medium that is capable of storing, encoding, or carrying instructions 816 for execution by the machine 800, and includes digital or analog communications signals or other intangible media to facilitate communication of such software.

Furthermore, the machine-readable medium 838 is non-transitory (in other words, not having any transitory signals) in that it does not embody a propagating signal. However, labeling the machine-readable medium 838 "non-transitory" should not be construed to mean that the medium is incapable of movement; the medium should be considered as being transportable from one physical location to another. Additionally, since the machine-readable medium 838 is tangible, the medium may be considered to be a machine-readable device.

Figure 9:
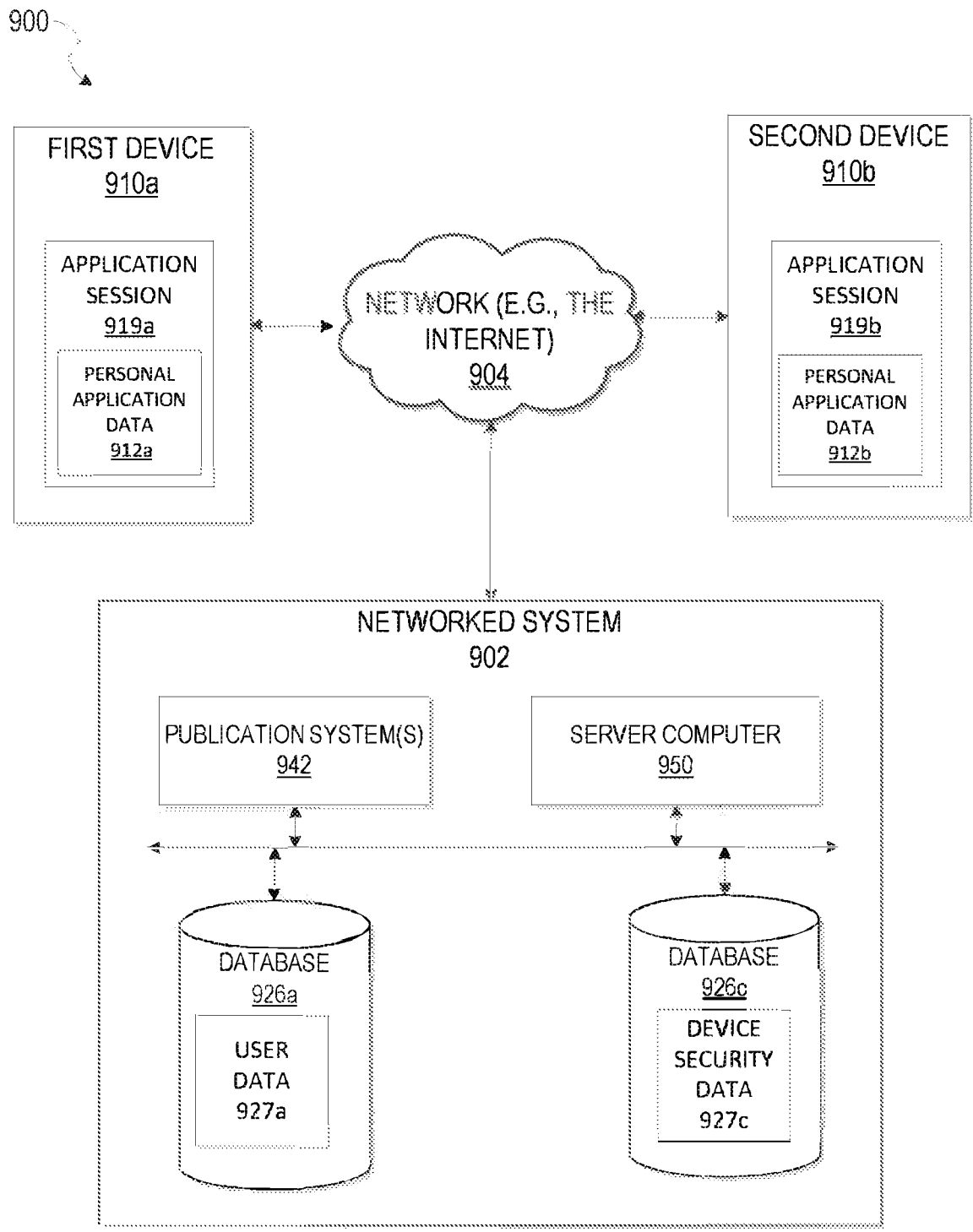
FIG. 9 illustrates a diagrammatic representation of a network which may be used with an implementation of a system for waist measurement using a waist measuring belt, according to certain example embodiments.

FIG. 9 is a block diagram illustrating a network architecture of a system 900 for communications between waist measuring belts, mobile devices, server computers, or any other such computing devices such as belt 100, mobile device 180, and server computer 106. The system 900 includes a first device 910*a*, second device 910*b*, and a networked system 902, which may communicate with each other through a network 904. The first device 910*a* and the second device 910*b* represent client devices and are also referred to as electronic devices. The first device 910*a* may be executing an application session 919*a* which may include personal application data 912*a* such as any form of waist measurement information or estimated waist size values. The second device 910*b* may be executing an application session 919*b* which may include personal application data 912*b*. The application session 919*a* running on the first device 910*a* may be transferred to the second device 910*b* and represented as the application session 919*b*, and vice versa, according to one embodiment.

Devices and network components operating as part of network 904 and networked system 902 may include any access point hardware, networking hardware, or communication device described herein which may be used to relay information between devices 910 and networked system 902, either of which may comprise a belt 100, mobile device 180, or server computer 106.

The networked system 902 includes a publication system(s) 942 and a server computer 950. The publication system(s) 942 and the server computer 950 access data stored in database 926*a*, which store user data, application data, and device security data. The data pertaining to the user account (also referred to as user data 927*a*) may be stored as one or more records in the database 926*a*. The data pertaining to the user account may include data identifying the user (e.g., the user's first and last names, phone number, billing and shipping address(es), and Social Security Number (SSN), whether the user is a frequent buyer, whether the user is also a vendor or a seller, etc.), transaction data (e.g., the name of a purchased product, a product identifier, the date of transaction, the price, the condition of the product, etc.), user demographic data (e.g., age, gender, financial information, family status, employment status, etc.), purchase history data, return history data, product review data, etc. The user data 927a may also include the user's login information such as user name and password.

In various example embodiments, one or more portions of the network 880 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the public switched telephone network (PSTN), a plain old telephone service (POTS) network, a cellular telephone network, a wireless network, a Wi-Fi® network, another type of network, or a combination of two or more such networks. For example, the network 880 or a portion of the network 880 may include a wireless or cellular network and the coupling 882 may be a Code Division Multiple Access (CDMA) connection, a Global System for Mobile communications (GSM) connection, or another type of cellular or wireless coupling. In this example, the coupling 882 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an application specific integrated circuit (ASIC). A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a particular processor or processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, with a particular processor or processors being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network 904 (e.g., the Internet) and via one or more appropriate interfaces (e.g., an application program interface (API)).

The performance of certain of the operations may be distributed among the processors, not only residing within a single machine, but deployed across a number of machines. In some example embodiments, the processors or processor-implemented modules may be located in a single geographic location (e.g., within a home environment, an office environment, or a server farm). In other example embodiments, the processors or processor-implemented modules may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A method comprising:
receiving, from a wearable device, tension data that indicates a plurality of tensions experienced during a time interval by a portion of the wearable device encompassing a waist of a user wearing the wearable device;
generating, based on the tension data, an estimated waist size for user;
receiving, from a server, a plurality of waist sizes, each of the plurality of waist sizes indicating a waist size for a different user measured during the time interval; and
causing a display of the estimated waist size for the user compared relative to at least a portion of the plurality of waist sizes at a client computing device.

2. The method of claim 1, wherein the wearable device is a belt and the portion of the wearable device encompassing the waist of the user is a belt strap, the method further comprising receiving position data from an attachment frame of the belt, position data that indicates one of a plurality of discrete attachment areas along the belt strap being used to mechanically couple the belt strap to the attachment frame, wherein generating the estimated waist size is further performed using the position data.

3. The method of claim 1, further comprising transmitting the estimated waist size for the user to the server independent of personally identifying information for the user.

4. The method of claim 1, further comprising receiving input at the client computing device setting a waist size threshold and causing output of an alert at the client computing device responsive to determining that the estimated waist size exceeds the waist size threshold.

5. The method of claim 1, further comprising receiving input at the client computing device designating a waist size threshold and causing a display of an achievement at the client computing device responsive to determining that the estimated waist size satisfies the waist size threshold.

6. The method of claim 1, wherein the wearable device and the client computing device are connected via a wireless communication connection and receiving the tension data is performed via the wireless communication connection.

7. The method of claim 1, wherein causing the display of the estimated waist size at the client computing device further comprises causing the estimated waist size to be displayed together with at least one historical waist size measurement for the user.

8. A system comprising:
one or more processors; and
a computer-readable medium storing instructions that are executable by the one or more processors to perform operations comprising:
receiving, from a wearable device, tension data that indicates a plurality of tensions experienced during a time interval by a portion of the wearable device encompassing a waist of a user wearing the wearable device;
generating, based on the tension data, an estimated waist size for user;
receiving, from a server, a plurality of waist sizes, each of the plurality of waist sizes indicating a waist size for a different user measured during the time interval; and
causing a display of the estimated waist size for the user compared relative to at least a portion of the plurality of waist sizes at a client computing device.

9. The system of claim 8, wherein the wearable device is a belt and the portion of the wearable device encompassing the waist of the user is a belt strap, the operations further comprising receiving position data from an attachment frame of the belt, position data that indicates one of a plurality of discrete attachment areas along the belt strap being used to mechanically couple the belt strap to the attachment frame, wherein generating the estimated waist size is further performed using the position data.

10. The system of claim 8, the operations further comprising transmitting the estimated waist size for the user to the server independent of personally identifying information for the user.

11. The system of claim 8, the operations further comprising receiving input at the client computing device setting a waist size threshold and causing output of an alert at the client computing device responsive to determining that the estimated waist size exceeds the waist size threshold.

12. The system of claim 8, the operations further comprising receiving input at the client computing device designating a waist size threshold and causing a display of an achievement at the client computing device responsive to determining that the estimated waist size satisfies the waist size threshold.

13. The system of claim 8, wherein the wearable device and the client computing device are connected via a wireless communication connection and receiving the tension data is performed via the wireless communication connection.

14. The system of claim 8, wherein causing the display of the estimated waist size at the client computing device further comprises causing the estimated waist size to be displayed together with at least one historical waist size measurement for the user.

15. A non-transitory computer-readable medium storing instructions that are executable by a computing device to perform operations comprising:
receiving, from a wearable device, tension data that indicates a plurality of tensions experienced during a time interval by a portion of the wearable device encompassing a waist of a user wearing the wearable device;
generating, based on the tension data, an estimated waist size for user;
receiving, from a server, a plurality of waist sizes, each of the plurality of waist sizes indicating a waist size for a different user measured during the time interval; and
causing a display of the estimated waist size for the user compared relative to at least a portion of the plurality of waist sizes at a client computing device.

16. The non-transitory computer-readable medium of claim 15, wherein the wearable device is a belt and the portion of the wearable device encompassing the waist of the user is a belt strap, the operations further comprising receiving position data from an attachment frame of the belt, position data that indicates one of a plurality of discrete attachment areas along the belt strap being used to mechanically couple the belt strap to the attachment frame, wherein generating the estimated waist size is further performed using the position data.

17. The non-transitory computer-readable medium of claim 15, the operations further comprising transmitting the estimated waist size for the user to the server independent of personally identifying information for the user.

18. The non-transitory computer-readable medium of claim 15, the operations further comprising receiving input at the client computing device setting a waist size threshold and causing output of an alarm at the client computing device responsive to determining that the estimated waist size exceeds the waist size threshold.

19. The non-transitory computer-readable medium of claim 15, the operations further comprising receiving input at the client computing device designating a waist size threshold and causing a display of an achievement at the client computing device responsive to determining that the estimated waist size satisfies the waist size threshold.

20. The non-transitory computer-readable medium of claim 15, wherein the wearable device and the client computing device are connected via a wireless communication connection and receiving the tension data is performed via the wireless communication connection.

* * * * *